(12) United States Patent
Solis (10) Patent No.: US 9,895,073 B2
(45) Date of Patent: Feb. 20, 2018

(54) DUAL BASKET CATHETER

(71) Applicant: BIOSENSE WEBSTER (ISRAEL) LTD., Yokneam (IL)

(72) Inventor: Mario A. Solis, Rancho Cucamonga, CA (US)

(73) Assignee: Biosense Webster (Israel) Ltd. (IL)

( * ) Notice: Subject to any disclaimer, the term of this patent is extended or adjusted under 35 U.S.C. 154(b) by 263 days.

(21) Appl. No.: 14/812,519

(22) Filed: Jul. 29, 2015

(65) Prior Publication Data

US 2017/0027638 A1    Feb. 2, 2017

(51) Int. Cl.

| | | |
|---|---|---|
| *A61B 5/042* | (2006.01) | |
| *A61B 18/14* | (2006.01) | |
| *A61B 5/00* | (2006.01) | |
| A61B 18/00 | (2006.01) | |
| A61B 17/00 | (2006.01) | |

(52) U.S. Cl.
CPC .......... *A61B 5/0422* (2013.01); *A61B 5/6858* (2013.01); *A61B 5/6859* (2013.01); *A61B 18/1492* (2013.01); *A61B 2017/00867* (2013.01); *A61B 2018/00267* (2013.01); *A61B 2018/00279* (2013.01); *A61B 2018/00375* (2013.01); *A61B 2018/00577* (2013.01); *A61B 2018/00839* (2013.01); *A61B 2218/002* (2013.01)

(58) Field of Classification Search
CPC ................ A61B 5/0422; A61B 5/6858; A61B 2018/00261; A61B 2018/00375; A61B 2018/00577; A61B 18/1492; A61B 5/6859
See application file for complete search history.

(56) References Cited

U.S. PATENT DOCUMENTS

| | | | |
|---|---|---|---|
| 5,239,724 A | 8/1993 | Salecker et al. | |
| 5,332,089 A | 7/1994 | Tillett et al. | |
| 5,365,926 A | 11/1994 | Desai | |
| 5,391,199 A | 2/1995 | Ben-Haim | |
| 5,484,118 A | 1/1996 | Fujimura et al. | |
| 5,618,612 A | 4/1997 | Gstrein | |
| 5,690,963 A | 11/1997 | Spargo et al. | |
| 5,769,077 A * | 6/1998 | Lindegren | A61N 1/056 600/373 |
| 5,772,590 A | 6/1998 | Webster, Jr. | |
| 6,064,905 A | 5/2000 | Webster, Jr. et al. | |
| 6,745,080 B2 * | 6/2004 | Koblish | A61B 18/1492 607/122 |

(Continued)

FOREIGN PATENT DOCUMENTS

WO    WO 96/05768 A1    2/1996

OTHER PUBLICATIONS

European Search Report dated Dec. 16, 2016 in corresponding European Patent Application No. 16181605.3.

(Continued)

*Primary Examiner* — Lee S Cohen
(74) *Attorney, Agent, or Firm* — Vincent J. Serrao (57) ABSTRACT

This disclosure is directed to a catheter having a basket-shaped electrode assembly at the distal end of the catheter body formed from a plurality of spines with electrodes. Each spine is deflectable outwards into an expanded configuration, so that the basket-shaped electrode assembly has a proximal basket area and a distal basket area with different equatorial diameters.

19 Claims, 4 Drawing Sheets

(56) References Cited

U.S. PATENT DOCUMENTS

| | | |
|---|---|---|
| 6,748,255 B2 | 6/2004 | Fuimaono et al. |
| 6,973,340 B2 | 12/2005 | Fuimaono et al. |
| 7,089,063 B2 | 8/2006 | Lesh et al. |
| 7,474,909 B2 | 1/2009 | Phan et al. |
| 7,655,005 B2* | 2/2010 | Bhola ............... A61B 18/1492 604/101.01 |
| 7,753,906 B2 | 7/2010 | Esposito |
| 8,337,492 B2* | 12/2012 | Kunis ............... A61B 18/1492 606/41 |
| 8,712,550 B2 | 4/2014 | Grunewald |
| 8,909,316 B2 | 12/2014 | Ng |
| 2002/0065455 A1 | 5/2002 | Ben-Haim et al. |
| 2003/0120150 A1 | 6/2003 | Govari |
| 2004/0059327 A1* | 3/2004 | Jenkins ............. A61B 18/1492 606/41 |
| 2004/0068178 A1 | 4/2004 | Govari |
| 2005/0273095 A1 | 12/2005 | Taimisto et al. |
| 2008/0234564 A1 | 9/2008 | Beatty et al. |
| 2013/0231659 A1 | 9/2013 | Hill et al. |
| 2014/0207136 A1 | 7/2014 | De La Rama et al. |
| 2014/0257069 A1 | 9/2014 | Eliason et al. |
| 2014/0276748 A1 | 9/2014 | Ku et al. |
| 2015/0011991 A1 | 1/2015 | Buysman et al. |
| 2015/0119876 A1 | 4/2015 | Willard |
| 2015/0157402 A1 | 6/2015 | Kunis et al. |

OTHER PUBLICATIONS

U.S. Appl. No. 13/860,921, filed Apr. 11, 2013.
U.S. Appl. No. 14/063,477, filed Oct. 25, 2013.

\* cited by examiner

DUAL BASKET CATHETER

FIELD OF THE PRESENT DISCLOSURE

This invention relates to electrophysiologic (EP) catheters, in particular, EP catheters for mapping and/or ablation in the heart.

BACKGROUND

Electrophysiology catheters are commonly-used for mapping electrical activity in the heart. Various electrode designs are known for different purposes. In particular, catheters having basket-shaped electrode arrays are known and described, for example, in U.S. Pat. Nos. 5,772,590, 6,748,255 and 6,973,340, the entire disclosures of each of which are incorporated herein by reference.

Basket catheters typically have an elongated catheter body and a basket-shaped electrode assembly mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body.

It is desirable that a basket assembly be capable of detecting in as few beats as possible, including a single beat, as much of the electrical function of the region in which the electrode assembly is deployed, such as the left or right atrium. Through such mapping, it may be possible to identify areas of the heart generating abnormal impulses. For example, atrial fibrillation results from improper control of the timing and sequence of muscle contractions associated with a heart beat. Instead of regular, coordinated electrical activity, disorganized electrical signals may impede heart function. Suitable treatments may include performing an ablation procedure, such as targeted ablation of myocardial tissue to treatment the cardiac arrhythmias. A catheter may be used to apply RF energy and create a lesion to break arrhythmogenic current paths in the cardiac tissue. One type of an ablation procedure is termed pulmonary vein isolation, in which tissue in the area adjacent the junction of the pulmonary veins and the left atrium is ablated. The resulting lesions may isolate irregular electrical signals originating in the area from spreading through the rest of the atrium and disrupting the patient's heart beat.

For these and other applications, it would be desirable to provide a catheter and a technique for accurately positioning the mapping and/or ablation electrodes at the ostium of the pulmonary veins. Similarly, it would also be desirable to stabilize the portion of the catheter carrying the electrodes at the intended location. Moreover, it would be desirable to perform the mapping and ablation functions with a single catheter to simplify access to the treatment area. Accordingly, the techniques of this disclosure as described in the following materials satisfy these and other needs.

SUMMARY

The present disclosure is directed to a catheter with an elongated catheter body having proximal and distal ends and at least one lumen therethrough and a basket-shaped electrode assembly at the distal end of the catheter body, the basket-shaped electrode assembly comprising a plurality of spines connected at their proximal and distal ends, each spine comprising at least one electrode and configured to deflect outwards into an expanded configuration, wherein the basket-shaped electrode assembly has a proximal basket area and a distal basket area having different equatorial diameters when the basket-shaped electrode assembly is in the expanded configuration.

In one aspect, the distal basket area may have a relatively smaller equatorial diameter than the proximal basket area.

In one aspect, each spine may have a proximal convex portion corresponding to the proximal basket area, a distal convex portion corresponding to the distal basket area and an intermediate concave portion separating the proximal convex portion and the distal convex portion.

In one aspect, each spine may have at least one sensing electrode. Alternatively or in addition, each spine may have at least one ablation electrode.

In one aspect, each spine may have a proximal sensing electrode, a distal sensing electrode and an ablation electrode positioned between the proximal sensing electrode and the distal sensing electrode. The proximal sensing electrode, the distal sensing electrode and the ablation electrode may be located at a distal end of the proximal basket area. In one embodiment, the basket-shaped electrode assembly comprises ten spines.

In one aspect, the catheter may include an expander having proximal and distal ends, the expander slidably disposed within the lumen and aligned with the longitudinal axis of the catheter body, wherein the plurality of spines are attached at their distal ends to the expander, such that the basket-shaped electrode assembly has a collapsed configuration when the expander is moved distally along the longitudinal axis relative to the catheter body and assumes the expanded configuration when the expander is move proximally along the longitudinal axis relative to the catheter body.

In one aspect, each spine may be formed from a shape memory alloy.

In one aspect, the lumen may be configured to deliver irrigation fluid to the basket-shaped electrode assembly.

This disclosure is also directed to a method for providing electrical communication with a heart by providing a catheter having an elongated catheter body with proximal and distal ends and at least one lumen therethrough and a basket-shaped electrode assembly at the distal end of the catheter body, the basket-shaped electrode assembly comprising a plurality of spines connected at their proximal and distal ends, each spine comprising at least one electrode and configured to deflect outwards into an expanded configuration, positioning the distal end of the catheter at a desired region of the heart and expanding the basket-shaped electrode assembly from a collapsed configuration wherein the spines are arranged generally along a longitudinal axis of the catheter body to an expanded configuration such that the basket-shaped electrode assembly has a proximal basket area and a distal basket area having different equatorial diameters when the basket-shaped electrode assembly is in the expanded configuration and at least one of the electrodes is brought into contact with tissue.

In one aspect, expanding the basket-shaped electrode assembly may cause the distal basket area to engage tissue in order to stabilize the basket-shaped electrode assembly.

In one aspect, expanding the basket-shaped electrode assembly may cause at least one electrode on the proximal basket area to contact tissue.

In one aspect, providing electrical communication may include recording electrical data received from the at least one electrode in contact with tissue.

In one aspect, providing electrical communication may include delivering radio frequency energy to the at least one electrode in contact with tissue to ablate the tissue and form a lesion.

In one aspect, positioning the distal end of the catheter at a desired region of the heart may include advancing the basket-shaped electrode assembly from a left atrium through an ostium and into a pulmonary vein. As such, expanding the basket-shaped electrode assembly may anchor the distal basket area within the pulmonary vein. Further, providing electrical communication may include delivering radio frequency energy to electrodes of the spines to form a substantially circumferentially lesion around the ostium of the pulmonary vein.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or 'map' this type of electrical activity, it is desirable to obtain the 'picture' as quickly as possible, such as within one heartbeat. In other words, all the points of the map or picture may be obtained simultaneously within one-tenth of a second. Further, radiofrequency energy may be delivered to pulmonary vein tissue in order to create one or more lesions to block electrical conduction and electrically isolate the pulmonary veins from the left atrium. Further, it may be desirable to form contiguous lesions in a circumferential manner around the pulmonary vein to minimize the migration of irregular electrical activity in the pulmonary vein to other areas of the atrium and cause fibrillation or other arrhythmias.

Thus, according to the techniques of this disclosure, a dual basket-shaped electrode assembly may feature at least two basket-shaped areas formed by the same plurality of spines. In particular, a first distal basket-shaped area may be configured to enter the pulmonary vein from the left atrium such that expansion of the basket-shaped electrode assembly anchors it within the vein. A second proximal basket-shaped area may remain in the left atrium adjacent the pulmonary vein ostium. Expansion of the basket-shaped electrode assembly may bring one or more electrodes into contact or closer proximity with the atrial and pulmonary vein tissue in order to communicate electrical signals by recording electrical signals generated by the heart and/or by delivering radio frequency energy to ablate tissue and form conduction blocking lesions.

Figure 1:
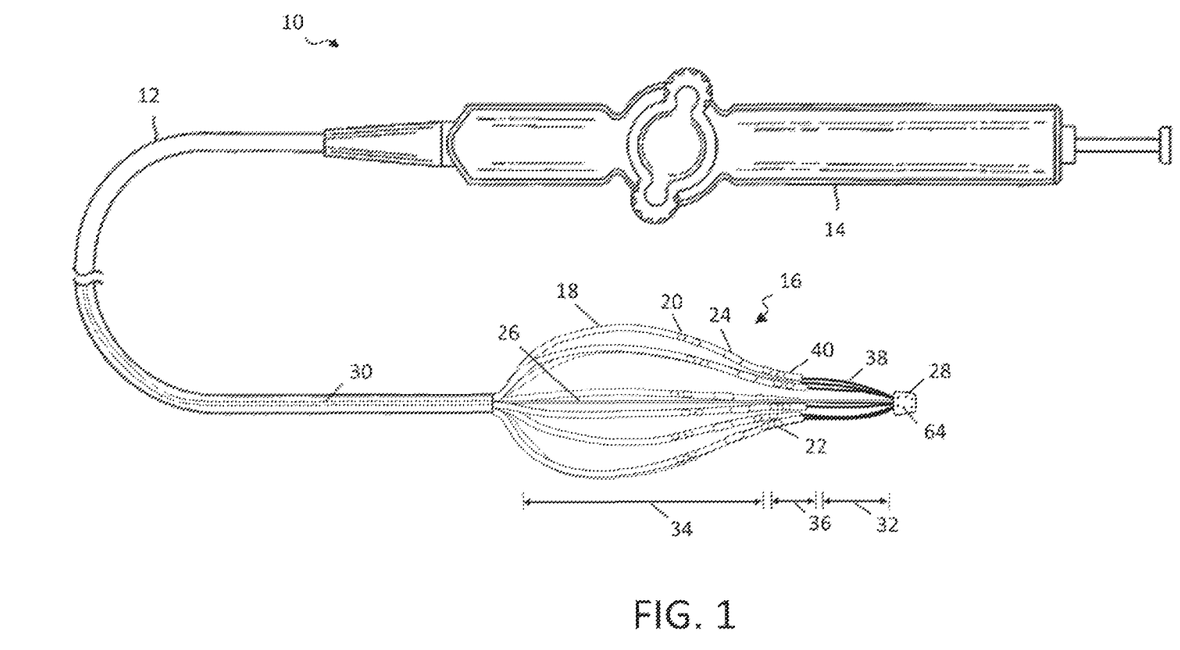
FIG. 1 is a top plan view of a catheter of the present invention, according to one embodiment.

As shown in FIG. 1, the catheter 10 comprises an elongated catheter body 12 having proximal and distal ends and a control handle 14 at the proximal end of the catheter body, with a basket-shaped electrode assembly 16 having a plurality of spines 18 mounted at the distal end of the catheter body 12, each of which may carry one or more electrodes. In this embodiment, each spine 18 may carry a set of proximal sensing electrodes 20 and a set of distal sensing electrodes 22. Further, each spine may also have at least one ablation electrode 24. The catheter body 12 comprises an elongated tubular construction having a single, axial or central lumen (not shown), but can optionally have multiple lumens if desired. Sensing electrodes 20 and 22 may be provided in a sufficient density to enable accurate mapping of electrical signals of the tissue adjacent the pulmonary vein ostium. Similarly, ablation electrodes 24 may also be provided in a density configured to form a blocking lesion, such as a substantially contiguous circumferential lesion around the pulmonary vein. Thus, the number of electrodes, including sensing electrodes 20 and 22 and ablation electrodes 24, may vary depending on the design of catheter 10. In this embodiment, each spine 18 may feature a pair of proximal sensing electrodes 20, a pair of distal sensing electrodes 24 and a single ablation electrode 24 as shown. In other designs, each spine 18 may include other numbers and types of electrodes and the electrodes may be evenly distributed along the spine or may be skewed proximally, centrally or distally to facilitate analysis of the measured electrical signals. Here, the distribution of proximal sensing electrodes 20, distal sensing electrodes 24 and ablation electrodes 24 may be adapted to the anticipated position of dual basket-shaped electrode assembly 16 at the pulmonary vein ostium as described below. Similarly, different numbers of spines 18 may be employed, such as from approximately eight to twelve, or any other suitable number. In one embodiment, ten spines 18 may be employed.

The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner. The outer diameter of the catheter body 12 is not critical, but generally should be as small as possible and may be no more than about 10 french depending on the desired application. Likewise the thickness of the outer wall is not critical, but may be thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

The dual basket-shaped electrode assembly 16 may also include an expander 26 is generally coaxial with the catheter body 12 and extends from the proximal end of catheter body 12 through the central lumen and is attached, directly or indirectly, to the distal ends of spines 18. The expander 26 is afforded longitudinal movement relative to the catheter body so that it can move the distal ends of the spines 18 proximally or distally relative to the catheter body 12 to radially expand and contract, respectively, the electrode assembly. Since the proximal ends of spines 18 are secured to the catheter body 12, relative movement of expander 26 in the proximal direction shortens the distance between the distal and proximal ends of spines 18, causing them to bow outwards into an expanded, dual basket arrangement. The expander 26 comprises a material sufficiently rigid to achieve this function. Alternatively or in addition, spines 18 may include a material as described below that facilitates assuming the expanded arrangement, such as a shape memory material, so that expander 26 may be omitted or may be used to aid the transition between the expanded and collapsed arrangements. In an embodiment, the expander 26 may comprise a wire or hypotube formed from a suitable shape memory material, such as a nickel titanium alloy as described below. As will be appreciated, different relative amounts of movement of the expander 26 along the longitudinal axis may affect the degree of bowing, such as to enable the spines 18 to exert greater pressure on the surrounding tissue for anchoring and/or better contact between the tissue and the electrodes on the spines. Thus, a user can modify the shape of the electrode assembly by adjusting the longitudinal extension or withdrawal of the expander.

The distal ends of the spines 18 and the expander 26 may be secured to a distal cap 28. Correspondingly, the proximal ends of the spines 18 may be secured to the distal end of the catheter body 12, while the expander 26 may be routed through lumen 30 of the catheter body 12 so that the proximal end extends to the control handle 14. In some embodiments, lumen 30 may also be used to supply a suitable irrigation fluid, such as heparinized saline, to the basket-shaped electrode assembly 16. A fitting (not shown) in the control handle 14 may be provided to conduct irrigation fluid from a suitable source or pump into the lumen 30.

Figure 2:
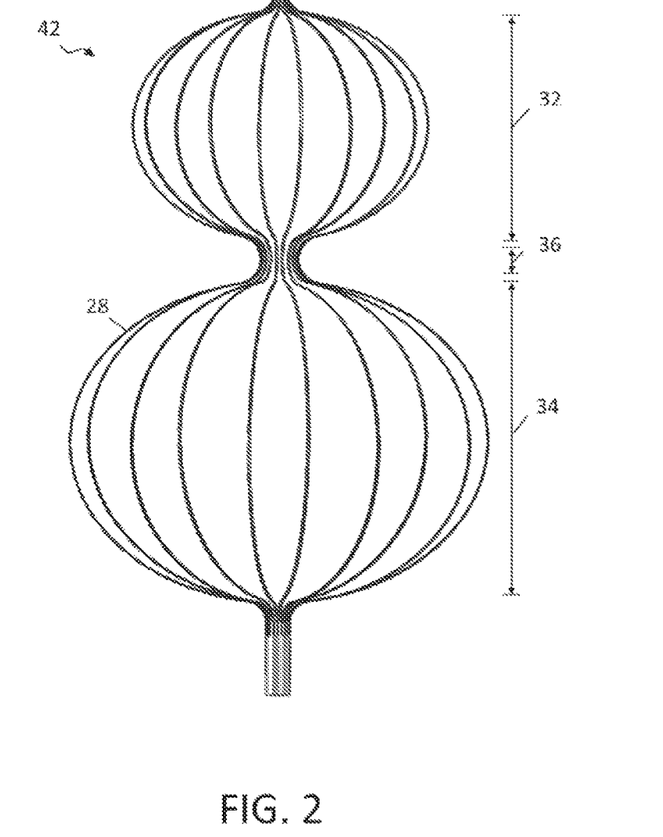
FIG. 2 is a schematic view of a frame for a dual basket-shaped electrode assembly, according to one embodiment.

As noted above, basket-shaped electrode assembly 16 may have a dual basket configuration when spines 18 are bowed outward by proximal movement of expander 26. A distal basket area may be formed by a distal convex portion 32 of each spine 18 while a proximal basket area may be formed by a proximal convex portion 34. Distal convex portion 32 may be separated from proximal convex portion 34 by an intermediate concave portion 36. In general, distal basket area may have an equatorial diameter that is relatively less than proximal basket area, so that distal basket area may be positioned within the pulmonary vein and expanded to secure basket-shaped electrode assembly 16 at its desired position. The relatively larger equatorial diameter of the proximal basket area may facilitate contact with atrial tissue adjacent the pulmonary vein ostium.

Each spine 18 may comprise a flexible wire 38 with a non-conductive covering 40 on which one or more of the ring electrodes 20 are mounted. In an embodiment, the flexible wires 28 may be formed from a shape memory material to facilitate the transition between expanded and collapsed arrangements and the non-conductive coverings 40 may each comprise a biocompatible plastic tubing, such as polyurethane or polyimide tubing. For example, nickel-titanium alloys known as nitinol may be used. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°-60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature. Accordingly, the basket-shaped electrode assembly 16 may have a three dimensional shape that can be easily collapsed to be fed into a guiding sheath and then readily returned to its expanded shape memory configuration upon delivery to the desired region of the patient upon removal of the guiding sheath.

Alternatively, in some embodiments the spines 18 can be designed without the internal flexible wire 38 if a sufficiently rigid nonconductive material is used for the non-conductive covering 40 to permit radial expansion of the basket-shaped electrode assembly 16, so long as the spine has an outer surface that is non-conductive over at least a part of its surface for mounting of the ring electrodes 20.

In one embodiment, flexible wires 38 of spines 18 may be formed by a shape memory frame 42. For example, shape memory frame 42 may be laser cut from a nitinol hypotube to form individual flexible wires 38. As noted above, the distal basket area may be formed by distal convex portion 32 and the proximal basket area may be formed by proximal convex portion 34. Intermediate concave portion 36 may separate distal convex portion 32 from proximal convex portion 34. The relatively smaller equatorial diameter of the distal basket area may be used to secure basket-shaped electrode assembly 16 within the pulmonary vein, while the relatively larger equatorial diameter of the proximal basket area may be deployed within the left atrium, to bring the electrodes into contact with tissue adjacent the pulmonary vein ostium.

Figure 3:
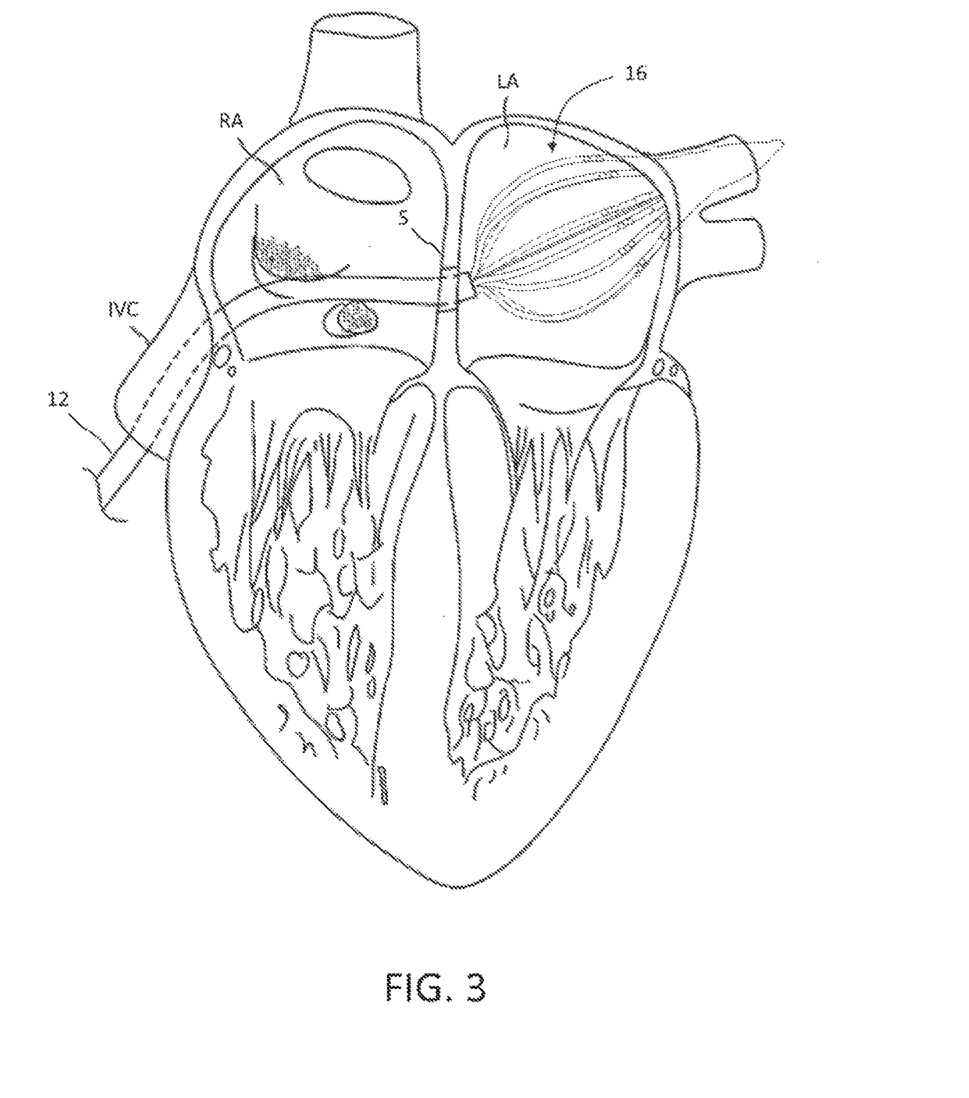
FIG. 3 is a schematic view of a dual basket-shaped electrode assembly in an expanded configuration within the left atrium and a pulmonary vein, according to one embodiment.

In one aspect, an electrophysiologist may introduce a guiding sheath, guidewire and dilator into the patient, as is generally known in the art, such as by the Seldinger technique that provides access for an introducer sheath through a peripheral vein, typically a femoral vein. Other suitable approaches include accessing the left atrium via the superior vena cava, or use of a retrograde intra-arterial technique. Examples of suitable guiding sheaths for use in connection with the inventive catheter are the PREFACE™ Braided Guiding Sheath (commercially available from Biosense Webster, Inc., Diamond Bar, Calif.) and the DiRex™ Guiding Sheath (commercially available from BARD, Murray Hill, N.J.). The guidewire is inserted, the dilator is removed, and the catheter is introduced through the guiding sheath whereby the guidewire lumen in the expander permits the catheter to pass over the guidewire. In one exemplary procedure as depicted in FIG. 3, the catheter is first introduced to the right atrium (RA) via the inferior vena cava (IVC), where it passes through a puncture in the fossa ovalis of the interatrial septum (S) in order to reach the left atrium (LA).

As will be appreciated, the guiding sheath covers the spines 18 of the basket-shaped electrode assembly 16 in a collapsed position so that the entire catheter can be passed through the patient's vasculature to the desired location. The expander 26 may be positioned distally of the catheter body to allow the spines of the assembly to be flattened while the assembly is passed through the guiding sheath. Once the distal end of the catheter reaches the desired location, e.g., the left atrium or the ostium of one of the two superior and the two inferior pulmonary veins, the guiding sheath is withdrawn to expose the basket-shaped electrode assembly 16. The expander 26 is drawn proximally to expand basket-shaped electrode assembly 16 so that the distal basket area engages the inner walls of the pulmonary vein to anchor or otherwise stabilize basket-shaped electrode assembly 16. Expansion of basket-shaped electrode assembly 16 also brings the proximal basket area into contact or closer proximity with atrial tissue adjacent the ostium.

Accordingly, proximal sensing electrodes 20 and distal sensing electrodes 22 may be used to record electrical activity associated with the pulmonary vein, to identify tissue to be ablated for example. Similarly, ablation electrodes 24 may be used to create lesions to electrically isolate the pulmonary vein from the left atrium. Placement of the sensing electrodes 20 and 22 and the ablation electrodes 24 longitudinally along each spine 18 may be adapted to bring them into contact with desired areas of tissue, based on the anticipated position of basket-shaped electrode assembly 16 relative to the treatment area. For example, the distal basket portion as well as a distal end of the proximal basket portion may be disposed within the pulmonary vein when basket-shaped electrode assembly 16 is stabilized. In one embodiment, sensing electrodes 20 and 22 and the ablation electrodes 24 may be located adjacent the junction between proximal convex portion 34 and intermediate concave portion 36, so that distal sensing electrodes 22 are at the distal end of proximal convex portion 34, at the proximal end of intermediate concave portion 36 or at the inflection between them. Correspondingly, ablation electrodes 24 and proximal sensing electrodes 20 may be positioned relatively more proximal. As a result of this placement, distal sensing electrodes 22 may be positioned within the pulmonary vein and in contact with the inner vessel wall to record electrical signals from the pulmonary vein. Likewise, ablation electrodes 24 may be in contact with the pulmonary vein ostium and proximal sensing electrodes 20 may be in contact with atrial tissue adjacent the ostium.

Since spines 18 may be distributed radially around catheter body 12, it may be possible to form a substantially contiguous circumferential lesion without repositioning basket-shaped electrode assembly 16. As desired, the mapping and/or ablation procedure may be repeated for other pulmonary veins. The order in which the specific pulmonary veins are visited and treated is arbitrary, but the two superior pulmonary veins have more prominent muscular sleeves and may provide greater effect. Typically, an ablation procedure may involve the isolation of all four pulmonary veins.

In a further aspect, each spine 18 may include cabling with built-in or embedded lead wires for the electrodes 20 carried by the spine as described in U.S. application Ser. No. 13/860,921, filed Apr. 11, 2013, entitled HIGH DENSITY ELECTRODE STRUCTURE, and U.S. application Ser. No. 14/063,477, filed Oct. 25, 2013, entitled CONNECTION OF ELECTRODES TO WIRES COILED ON A CORE, the entire disclosures of which are hereby incorporated by reference.

Figure 4:
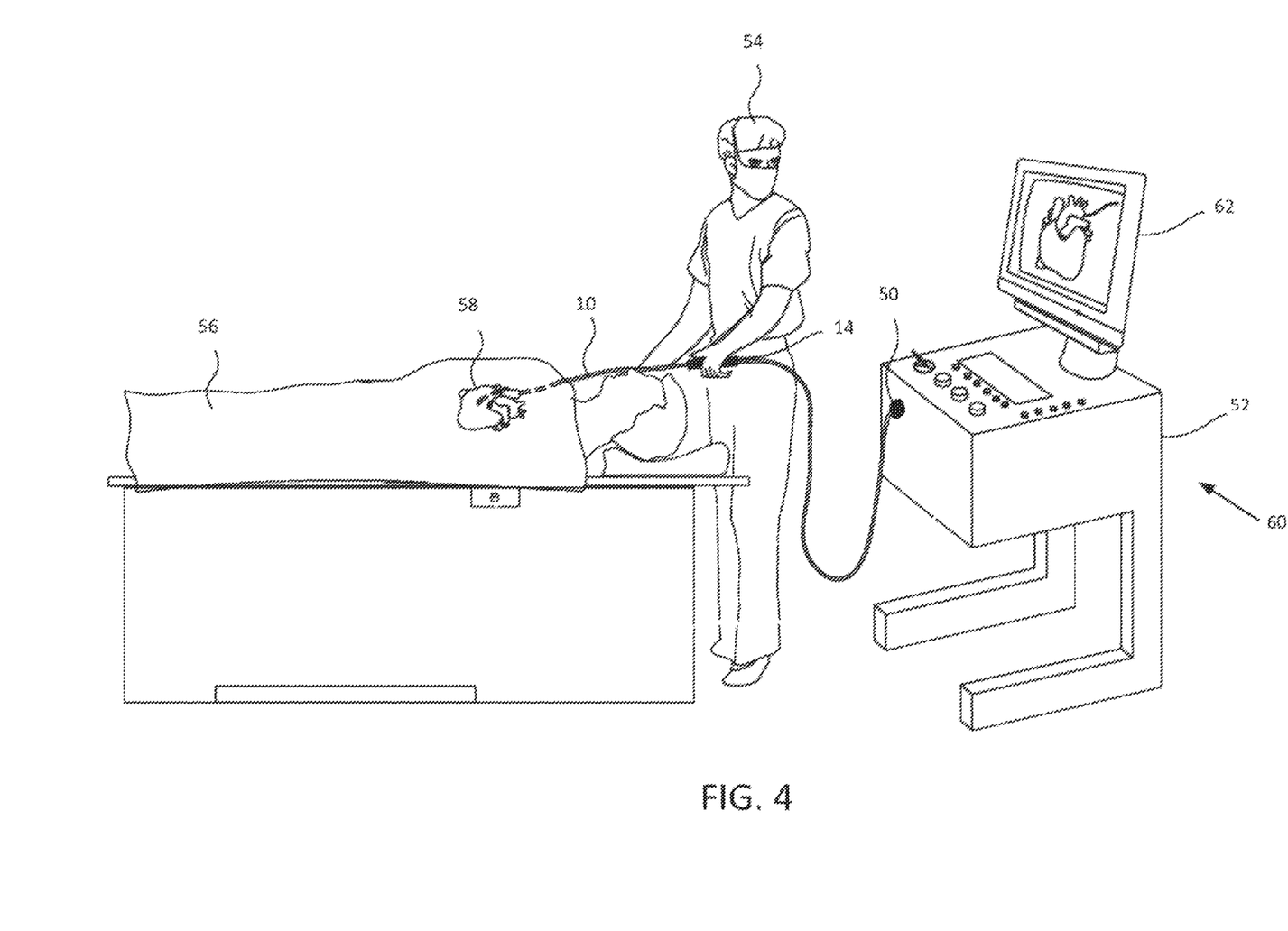
FIG. 4 is a schematic illustration of an invasive medical procedure using a dual basket-shaped electrode assembly, according to one embodiment.

To help illustrate use of the basket-shaped electrode assembly 16, FIG. 4 is a schematic depiction of an invasive medical procedure, according to an embodiment of the present invention. Catheter 10, with the basket-shaped electrode assembly 16 (not shown in this view) at the distal end may have a connector 50 at the proximal end for coupling the wires from their respective electrodes to a console 52 for recording and analyzing the signals they detect and/or for supplying radio frequency energy to ablate tissue. An electrophysiologist 54 may insert the catheter 10 into a patient 56 in order to acquire electropotential signals from the heart 58 of the patient. The professional uses the control handle 14 attached to the catheter in order to perform the insertion. Console 52 may include a processing unit 60 which analyzes the received signals, and which may present results of the analysis on a display 62 attached to the console. The results are typically in the form of a map, numerical displays, and/or graphs derived from the signals. Processing unit 60 may also control delivery of radio frequency energy. Still further, processing unit 60 may operate a pump to supply irrigation fluid though lumen 30.

In a further aspect, the processing unit 60 may also receive signals from one or more location sensors 64 provided near a distal end of the catheter 10 adjacent the basket-shaped electrode assembly 16 as schematically indicated in FIG. 1. The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 60 to determine the position, (e.g., the location and orientation) of the distal end of catheter 10 within the heart cavity. The electrophysiologist may then view the position of the basket-shaped electrode assembly 16 on an image the patient's heart on the display 62. By way of example, this method of position sensing may be implemented using the CARTO™ system, produced by Biosense Webster Inc. (Diamond Bar, Calif.) and is described in detail in U.S. Pat. Nos. 5,391,199, 5,690,963, 5,484,118, 5,239, 724, 5,618,612 and 5,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally of the basket-shaped electrode assembly 16. The coordinates of the distal sensor relative to the proximal sensor may be determined and, with other known information pertaining to the curvature of the spines 18 of the basket-shaped electrode assembly 16, used to find the positions of each of the electrodes 20.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising an elongated catheter body having proximal and distal ends and at least one lumen therethrough and a basket-shaped electrode assembly at the distal end of the catheter body, the basket-shaped electrode assembly comprising a plurality of spines made from a shape memory material, each spine having a preformed basket-shaped expanded configuration and being connected at their proximal and distal ends, each spine comprising at least one electrode and configured to deflect outwards into the preformed expanded configuration, wherein the basket-shaped electrode assembly has a proximal basket area and a distal basket area each formed by the same plurality of spines, and each having different equatorial diameters when the basket-shaped electrode assembly is in the expanded configuration.

2. The catheter of claim 1, wherein the distal basket area has a relatively smaller equatorial diameter than the proximal basket area.

3. The catheter of claim 1, wherein each spine has a proximal convex portion corresponding to the proximal basket area, a distal convex portion corresponding to the distal basket area and an intermediate concave portion separating the proximal convex portion and the distal convex portion.

4. The catheter of claim 1, wherein each spine comprises at least one sensing electrode.

5. The catheter of claim 1, wherein each spine comprises at least one ablation electrode.

6. The catheter of claim 1, wherein each spine comprises a proximal sensing electrode, a distal sensing electrode and an ablation electrode positioned between the proximal sensing electrode and the distal sensing electrode.

7. The catheter of claim 6, wherein the proximal sensing electrode, the distal sensing electrode and the ablation electrode are located at a distal end of the proximal basket area.

8. The catheter of claim 6, wherein the basket-shaped electrode assembly comprises ten spines.

9. The catheter of claim 1, further comprising an expander having proximal and distal ends, the expander slidably disposed within the lumen and aligned with the longitudinal axis of the catheter body, wherein the plurality of spines are attached at their distal ends to the expander, such that the basket-shaped electrode assembly has a collapsed configuration when the expander is moved distally along the longitudinal axis relative to the catheter body and assumes the expanded configuration when the expander is move proximally along the longitudinal axis relative to the catheter body.

10. The catheter of claim 1, wherein each spine comprises a shape memory alloy.

11. The catheter of claim 1, wherein the lumen is configured to deliver irrigation fluid to the basket-shaped electrode assembly.

12. A method for providing electrical communication with a heart comprising:
providing a catheter having an elongated catheter body with proximal and distal ends and at least one lumen therethrough and a basket-shaped electrode assembly at the distal end of the catheter body, the basket-shaped electrode assembly comprising a plurality of spines made from a shape memory material, each spine having a preformed basket-shaped expanded configuration and being connected at their proximal and distal ends, and configured such that the basket-shaped electrode assembly has a proximal basket area and a distal basket area having different equatorial diameters when the basket-shaped electrode assembly is in the expanded configuration, each of the proximal basket area and the distal basket area being formed by the same plurality of spines, each spine comprising at least one electrode and configured to deflect outwards into an expanded configuration;
positioning the distal end of the catheter at a desired region of the heart; and
expanding the basket-shaped electrode assembly from a collapsed configuration wherein the spines are arranged generally along a longitudinal axis of the catheter body to the expanded configuration such that at least one of the electrodes is brought into contact with tissue.

13. The method of claim 12, wherein expanding the basket-shaped electrode assembly causes the distal basket area to engage tissue in order to stabilize the basket-shaped electrode assembly.

14. The method of claim 12, wherein expanding the basket-shaped electrode assembly causes at least one electrode on the proximal basket area to contact tissue.

15. The method of claim 12, wherein providing electrical communication comprises recording electrical data received from the at least one electrode in contact with tissue.

16. The method of claim 12, wherein providing electrical communication comprises delivering radio frequency energy to the at least one electrode in contact with tissue to ablate the tissue and form a lesion.

17. The method of claim 12, wherein positioning the distal end of the catheter at a desired region of the heart comprises advancing the basket-shaped electrode assembly from a left atrium through an ostium and into a pulmonary vein.

18. The method of claim 17, wherein expanding the basket-shaped electrode assembly anchors the distal basket area within the pulmonary vein.

19. The method of claim 18, wherein providing electrical communication comprises delivering radio frequency energy to electrodes of the spines to form a substantially circumferential lesion around the ostium of the pulmonary vein.

\* \* \* \* \*